(12) United States Patent
Wahlstrand et al.

(10) Patent No.: US 8,694,123 B2
(45) Date of Patent: Apr. 8, 2014

(54) HELICAL ELECTRODE ARRANGEMENTS FOR MEDICAL LEADS

(75) Inventors: Carl D. Wahlstrand, North Oaks, MN (US); Dale F. Seeley, Spring Park, MN (US); Gabriela C. Molnar, Fridley, MN (US); Lisa M. Johanek, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/376,117

(22) PCT Filed: Jun. 21, 2010

(86) PCT No.: PCT/US2010/039295
§ 371 (c)(1),
(2), (4) Date: Dec. 2, 2011

(87) PCT Pub. No.: WO2010/148376
PCT Pub. Date: Dec. 23, 2010

(65) Prior Publication Data
US 2012/0078332 A1    Mar. 29, 2012

Related U.S. Application Data

(60) Provisional application No. 61/218,458, filed on Jun. 19, 2009.

(51) Int. Cl.
*A61N 1/05* (2006.01)
(52) U.S. Cl.
USPC ............................................ 607/116; 600/373
(58) Field of Classification Search
USPC ............................................ 607/116; 600/373
See application file for complete search history.

(56) References Cited

U.S. PATENT DOCUMENTS

| | | | |
|---|---|---|---|
| 3,804,098 A * | 4/1974 | Friedman | 607/122 |
| 4,774,952 A | 10/1988 | Smits | |
| 5,843,148 A * | 12/1998 | Gijsbers et al. | 607/116 |
| 7,515,968 B2 | 4/2009 | Metzler et al. | |
| 7,672,734 B2 | 3/2010 | Anderson | |
| 7,769,472 B2 | 8/2010 | Gerber | |
| 7,930,038 B2 * | 4/2011 | Zarembo | 607/116 |
| 7,996,092 B2 | 8/2011 | Mrva et al. | |
| 2004/0117728 A1 | 6/2004 | Gromer | |
| 2010/0114280 A1 * | 5/2010 | Hill et al. | 607/116 |
| 2010/0137959 A1 * | 6/2010 | Seifert | 607/116 |

OTHER PUBLICATIONS

PCT/US10/039294: Search Report and Written Opinion dated Oct. 6, 2010.
PCT/US10/039297: Search Report and Written Opinion dated Oct. 6, 2010.
PCT/US10/039295: Search Report and Written Opinion dated Oct. 11, 2010.

* cited by examiner

*Primary Examiner* — Christopher D Koharski
*Assistant Examiner* — Michael Carey (57) ABSTRACT

A medical lead includes a lead body having a proximal end for electrical connection to an implantable electric signal generator and a distal end portion having a plurality of electrodes extending in a helical manner longitudinally along the distal end portion. Adjacent helical electrodes may be offset, for example, 90 degrees or 180 degrees. The helical electrodes may extend less than, greater than, or 360 degrees. The electrode arrangement provides increased surface area, improving the capability of positioning the lead against the nerve as desired.

20 Claims, 5 Drawing Sheets

HELICAL ELECTRODE ARRANGEMENTS FOR MEDICAL LEADS

RELATED APPLICATION

This application is a U.S. National Stage filing under 35 U.S.C. 371 copending PCT Application Serial No. PCT/US2010/039295, filed Jun. 21 2010, which claims the benefit of priority to U.S. provisional patent application No. 61/218,458, filed Jun. 19, 2009, both of which applications are incorporated herein by reference to the extent that they do not conflict with the present disclosure.

FIELD

This disclosure relates to implantable medical devices. More particularly, it relates to implantable medical leads.

BACKGROUND

Many implantable medical devices, such as neurostimulators, pacemakers and defibrillators, transmit electrical signals to provide therapy to a patient. Electrical signals generated by the devices may be delivered to the tissue of a patient via one or more electrodes disposed at a distal end portion of a medical lead, which may be connected to the signal generator with a lead extension.

Typically nervous tissue is targeted by the electrical signals. In some cases the target may be a specific nerve fiber. In other cases the target may be specific nerve fascicles. In contrast, broad targeting of a nerve can have undesired consequences. For example, if a nerve is targeted for treatment of pain, selective targeting of afferent fibers, as opposed to efferent fibers, would be desired to avoid undesired motor side effects. Accordingly, targeting selected fascicles of a nerve would be preferred over broad targeting of the nerve.

However, such selective targeting of nerve fascicles can be difficult, as the fascicles do not often run in a nerve through a straight line. A lead having electrode configurations capable of facilitating selective capture of desired fascicles of a nerve would be desirable.

SUMMARY

The present disclosure describes, among other things, implantable medical leads having electrode configurations that can facilitate selective application of electrical signals to desired nerve fascicles. The leads have a plurality of electrodes extending in a helical manner longitudinally along the distal end portion of the lead body. Adjacent helical electrodes may longitudinally overlap, be offset by desired amounts, and extend desired amounts around the leads. Such leads may improve the likelihood that an electrical field generated via one or more of the helical electrodes will selectively capture a desired fascicle of a nerve. Such leads may be advantageously used for treating pain, where afferent fibers are desirably selectively stimulated. For example, such leads may be desirably used for treatment of pain via peripheral nerve stimulation.

In various embodiments, an implantable medical lead has a (i) lead body having a proximal end for electrical connection to an implantable electric signal generator and a distal end portion; and (ii) at least one helical electrode at the distal end portion of the lead body. The helical electrode may extend 180 degrees to 720 degrees around the lead body.

In some embodiments, an implantable medical lead has a first helical electrode and a second helical electrode. Each helical electrode has a first end and a second end defining a break having a longitudinal distance greater than zero.

In numerous embodiments, the electrodes are arranged so that any circumferential line drawn around the lead body in an area containing helical electrodes will intersect at least one electrode.

In some embodiments, the electrodes are arranged so that at least one circumferential line in the electrode area on the distal end portion will intersect at least two electrodes.

These and various other features and advantages will be apparent from a reading of the following detailed description.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the devices, systems and methods described herein. The following detailed description, therefore, is not to be taken in a limiting sense.

All scientific and technical terms used herein have meanings commonly used in the art unless otherwise specified. Any definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. It will be further understood that directional terms, such as "longitudinal", "lateral", "transverse", and the like, when used with regard to a lead, are intended to have approximate practical meanings in view of the limp structure of exemplary preferred leads and the environment of use, rather than precise geometrical meanings.

The recitation herein of numerical ranges by endpoints includes all numbers subsumed within that range (e.g., 1 to 5 includes at least 1, 1.5, 2, 2.75, 3, 3.80, 4 and 5) and any range within that range.

As used herein, "representative," "exemplary," and the like are used in the context of "providing an example" and do not necessarily indicate that the example provided is superior to, or more particularly suited for the intended purpose than, other potential examples.

The present disclosure describes, among other things, implantable medical leads having electrode configurations that can facilitate selective application of electrical signals to desired nerve fascicles. The leads have a plurality of electrodes extending in a helical manner longitudinally along the distal end portion of the lead body. Adjacent helical electrodes may longitudinally overlap, be offset by desired amounts, and extend desired amounts around the leads. Such leads may improve the likelihood that an electrical field generated via one or more of the helical electrodes will selectively capture a desired fascicle of a nerve. Such leads may be advantageously used for treating pain, where afferent fibers are desirably selectively stimulated. For example, such leads may be desirably used for treatment of pain via peripheral nerve stimulation.

It will be understood, however, that the leads described herein may be used with any electrical medical device, such as an electrical signal generator for neurological, cardiac, or gastric stimulation or a monitoring device for any suitable purpose.

Figure 1:
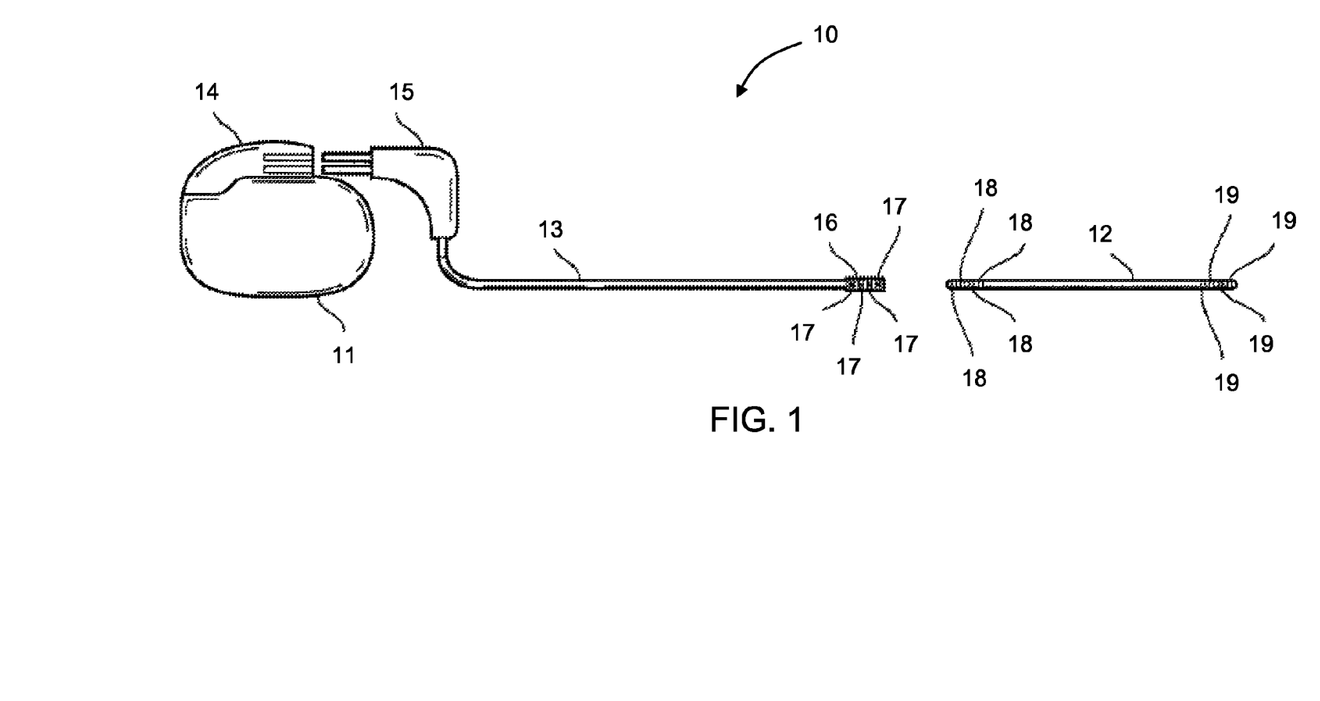
FIG. 1 is a diagrammatic representation of a side view of a representative stimulation system, illustrating a generic lead.

Referring to FIG. 1, a schematic side view of an embodiment of a representative system 10 is shown. System 10 includes an implantable electrical signal generator 11, a lead extension 13 and a lead 12. Implantable electrical signal generator 11 includes a connector header 14 configured to receive plug 15 at proximal end of lead extension 13 or other adaptor to operably couple lead 12 to electrical signal generator 11. The distal end portion of lead extension 13 includes a connector 16 configured to receive proximal end portion of lead 12. Connector 16 includes electrical contacts 17 configured to electrically couple extension 13 to lead 12 via electrical contacts 18 on the proximal end portion of lead 12. Electrodes 19 are present on distal end portion of lead 12 and are electrically coupled to electrical contacts 18, typically through conductors (not shown) within lead 12. In general, lead 12 may include any number of electrodes 19, e.g. one, two, three, four, five, six, seven, eight, sixteen or any other number. In some embodiments, each electrode 19 is electrically coupled to a discrete electrical contact 18, whereas in other embodiments, a set of electrodes 19 is electrically coupled to a discrete contact 18. While not shown, it will be understood that more than one lead 12 may be operably coupled to one electrical signal generator 11 or one extension 13 or that more than one extension 13 may be operably coupled to one electrical signal generator 11. It will be further understood that lead 12 may be coupled to electrical signal generator 11 without use of extension 13 or other adaptor.

The lead 12 depicted in FIG. 1 is shown for purposes of illustration of a lead in a system. The leads described in more detail herein have various arrangements of helical electrodes. As used herein, "helix", "helical" and the like, as they relate to an electrode, means an electrode that curves along the surface of a lead body, where the curve has a longitudinal vector and a circumferential vector.

In some embodiments, any transverse line perpendicular to the longitudinal axis of the lead body (i.e., a line around the circumference of the lead body, or a "circumferential line"), at an area of the lead body having electrodes will intersect at least one electrode. For example, "an area of the lead body having electrodes" may be defined as the portion of the lead body from the most proximal end of the most proximal electrode to the most distal end of the most distal electrode. In some embodiments, at least one or more circumferential lines will intersect two or more electrodes.

Referring now to FIGS. 2 through 6, various embodiments of leads, or portions thereof, having helical electrodes that including both a longitudinal aspect and a circumferential aspect are shown. In some embodiments, the electrode extends circumferentially 360 degrees around the lead body; in other embodiments, the electrode extends less than 360 degrees (e.g., about 180-360 degrees, in some embodiments 270-360 degrees), whereas in yet other embodiments, the electrode extends more than 360 degrees (e.g., about 360-720 degrees, in some embodiments, 360-540 degrees, in other embodiments 360-450 degrees).

Figure 2:
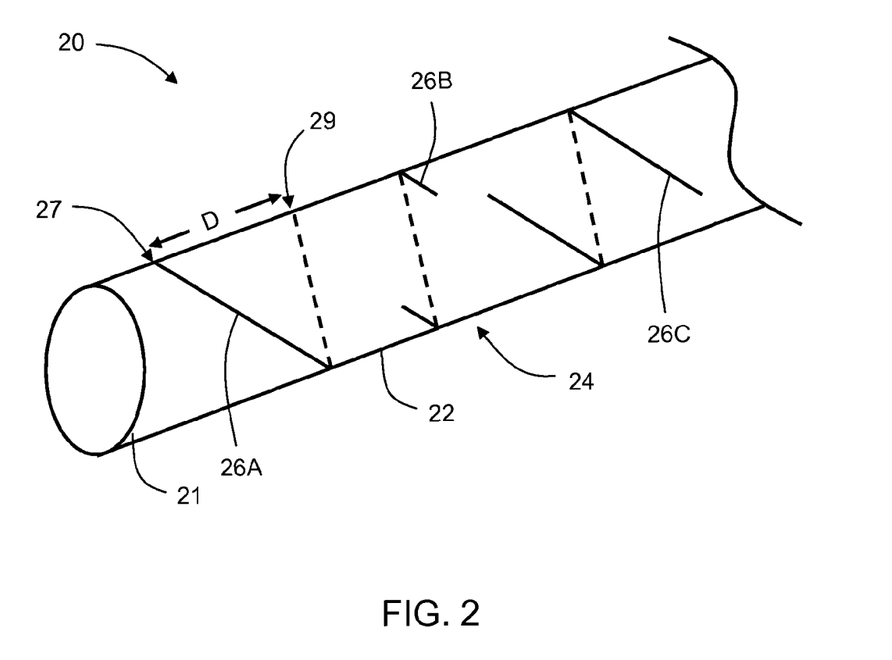
FIG. 2 is a schematic perspective view of an embodiment of a distal end portion of a lead.

Referring now particularly to FIG. 2, a distal end portion 24 of a lead 20 is illustrated having a lead body 21 with a proximal end (not illustrated). Lead body 21 has an outer surface 22, and in the depicted embodiment, lead body 21 has essentially the same shape and size along the length of the distal end portion 24, and may have the same shape and size its entire length. Of course, distal end portion 24 may have a larger or smaller diameter than the rest of body 21. Typically lead body 21 and distal end 24 are generally cylindrical and have a circular or nearly circular (i.e., constant radius within 10%) cross-sectional area. Exposed at the surface 22 of distal end portion 24 are a plurality of electrodes 26 (specifically electrodes 26A, 26B, 26C), with portions of the electrodes 26 on the back side of the lead 20 are shown in dashed lines. Each electrode 26 may be separately electrically connected to an electrode contact (not illustrated) positioned at or near the proximal end of lead 20. In some embodiments, multiple electrodes are electrically coupled to the same electrode contact.

Electrodes 26 include both a longitudinal aspect and a circumferential aspect; that is, electrodes 26 extend longitudinally and wrap around distal end portion 24. Referring to electrode 26A, the electrode has a first end 27 more distal than a second end 29, which is proximal in relation to first end 27. The length of electrode 26A is the distance from first end 27 to second end 29, taken along the path of the electrode. There is also a longitudinal distance of electrode 26A, defined by the distance in the direction of the longitudinal axis of the lead body that is spanned from the second end 29 to the first end 27. The longitudinal distance between end 27 and end 29 is indicated as D in FIG. 2. In most embodiments, this longitudinal distance is at least 0.1 mm and in some embodiments at least 0.2 mm. This distance may depend, for example, on the width of the electrode, the length of the electrode, and the helical angle of the electrode. For helical electrodes, as electrode 26A, the electrode length is more than the longitudinal distance. Also for helical electrodes, the electrode length is more than the circumferential distance of the electrode (taken perpendicular to lead body 21).

The three helical electrodes 26 of FIG. 2, i.e., electrodes 26A, 26B, 26C illustrate three potential configurations. Electrode 26A extends 360 degrees around distal end portion 24; electrode 26A would form a continuous ring if the longitudinal aspect of electrode 26A were removed. Electrode 26B extends less than 360 degrees around distal end portion 24; electrode 26B would not form a continuous ring if the longitudinal aspect of electrode 26B were removed. Electrode 26C extends greater than 360 degrees around distal end portion 24; electrode 26C would form a continuous ring with a length of overlap, if the longitudinal aspect of electrode 26C were removed. However, each of electrodes 26A, 26B, 26C span a longitudinal distance D that, in part, defines the helical nature of the electrode.

Electrodes 26A, 26B, 26C can have a helix angle (i.e., the angle between the helix and the axis of lead body 21) from about 10 degrees to 80 degrees, but in most embodiments is between about 22.5 degrees and 67.5 degrees. Specific examples of suitable helix angles include 45 degrees, 60 degrees, and 75 degrees. In most embodiments, the helix angle for all electrodes 26A, 26B, 26C on lead 20 is the same. Electrodes 26A, 26B, 26C may have an inter-electrode spacing (in the longitudinal direction) from about 0.5 mm to about 5 mm, although smaller and larger spacings could be used. Specific examples of suitable inter-electrode spacing include about 2 mm, about 3 mm, 3.8 mm, and about 4 mm. Inter-electrode distance may be determined by the longitudinal distance between a proximal end of one electrode and a distal end of an adjacent electrode, or in some cases the longitudinal distance between a proximal (or distal) end of one electrode and the proximal (or distal) end of an adjacent electrode.

Figure 3:
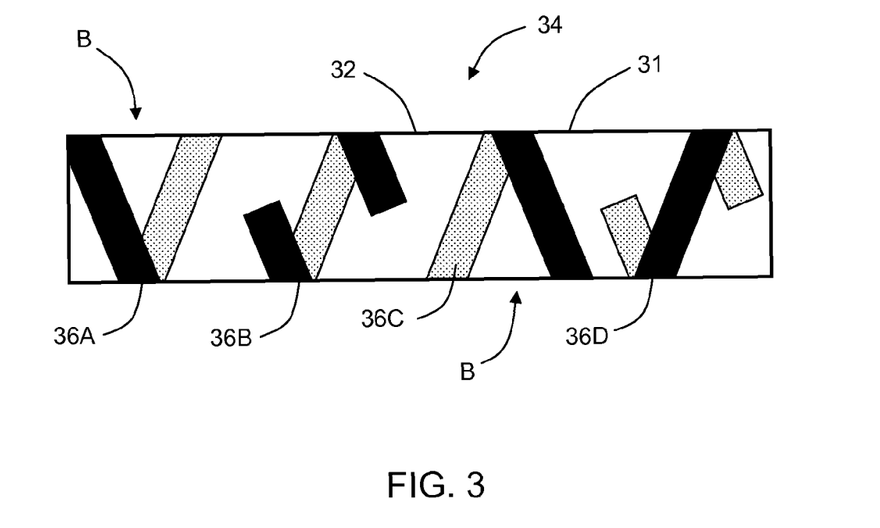
FIG. 3 is a schematic side view of an embodiment of a distal end portion of a lead.

FIG. 3 illustrates a possible arrangement of helical electrodes on a lead. FIG. 3 shows a distal end portion 34 of a lead, formed by a lead body 31 having a surface with a plurality of electrodes 36 thereon or exposed therethrough. In the depicted embodiment, individually arranged electrodes 36A, 36B, 36C, 36D are shown. Each of the depicted electrodes 36A, 36B, 36C, 36D circumferentially extend 360 degrees around the lead body, with a quarter-turn or 90 degrees between the break. That is, the most distal end of electrode 36B is located along the lead body along a longitudinal line defined by where the most proximal end of electrode 36A would end if it extended another 90 degrees around the lead at a constant angle; the most distal end of electrode 36C is located along a longitudinal line defined by where the most proximal end of electrode 36B would end if it extended another 90 degrees around the lead at a constant angle; and so on. Each of the electrodes 36A, 36B, 36C, 36D in the depicted embodiment extend around the lead body 31 at the same angle and have the same length. The view in FIG. 3 is a plan side view of distal end portion 34, with stippled areas indicating portions of electrodes on the back side of the lead. Electrode 36A wraps around body 31 one complete turn (360 degrees) from the complete front side to the complete back side. The break in electrode 36A is at the top of body 31, indicated as B. Adjacent electrode 36B wraps around body 31 one complete turn (360 degrees) from the lower half of the front side to the complete back side and back to the upper half of the front side, so that the break (not indicated) is in the center of the front side. Next electrode 36C wraps around body 31 one complete turn (360 degrees) from the complete back side to the complete front side; break B for electrode 36C is at the bottom of body 31. The final electrode 36D wraps around body 31 one complete turn (360 degrees) from the lower half of the back side to the complete front side and back to the upper half of the back side, so that the break (not indicated) is in the center of the back side.

Figure 4:
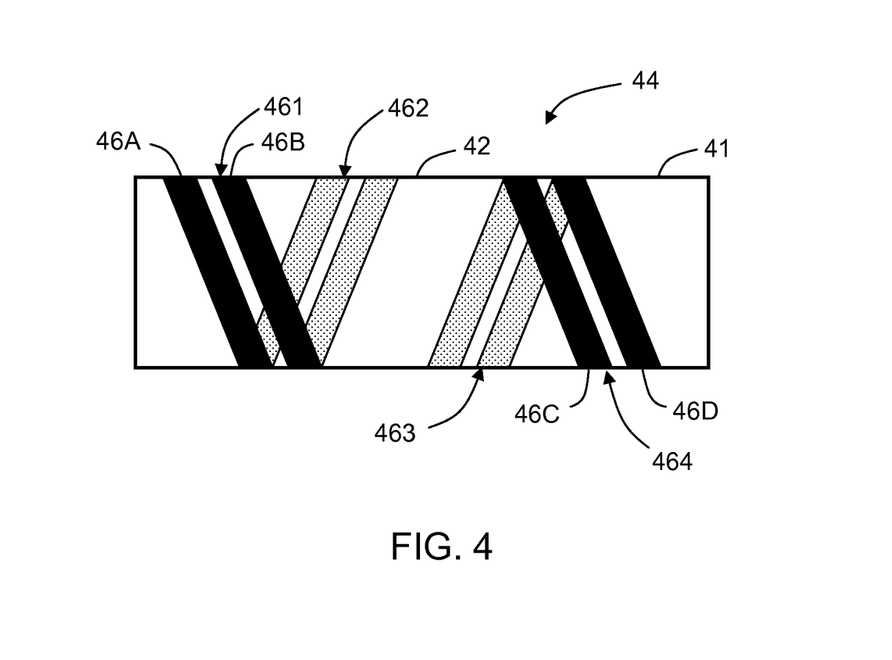
FIG. 4 is a schematic side view of an embodiment of a distal end portion of a lead.

FIG. 4 illustrates another possible arrangement of helical electrodes on a lead. FIG. 4 shows a distal end portion 44 of a lead, formed by a lead body 41 having surface 42 with a plurality of electrodes 46 thereon, in this embodiment, four electrodes 46A, 46B, 46C, 46D arranged as pairs 46A, 46B and 46C, 46D that are offset a half-turn or 180 degrees. Electrodes 46A, 46B may be electrically connected to the same contact or may be separately connected to discrete contacts. Similarly, electrodes 46C, 46D may be electrically connected to the same contact or may be connected separately to discrete contacts. Similar to FIG. 3, the view in FIG. 4 is a plan side view of distal end portion 44, with stippled areas indicating portions of the electrodes on the back side of the lead. Electrode pair 46A, 46B wraps around body 41 one complete turn (360 degrees) from the complete front side to the complete back side, so that the break for each of electrodes 46A, 46B is at the top of body 41. The adjacent electrode pair 46C, 46D wraps around body 41 one complete turn (360 degrees) from the complete back side to the complete front side, so that the break for each electrode 46C, 46D is at the bottom of body 41. In the depicted embodiment, a circumferential line drawn around the lead body 41 anywhere between the distal most end 461 of electrode 46B and the proximal most end 462 of electrode 46A would intersect both electrodes 46A and 46B. Similarly, a circumferential line anywhere between the distal most end 463 of electrode 46D and the proximal most end 464 of electrode 46C would intersect both electrodes 46C and 46D.

Figure 5:
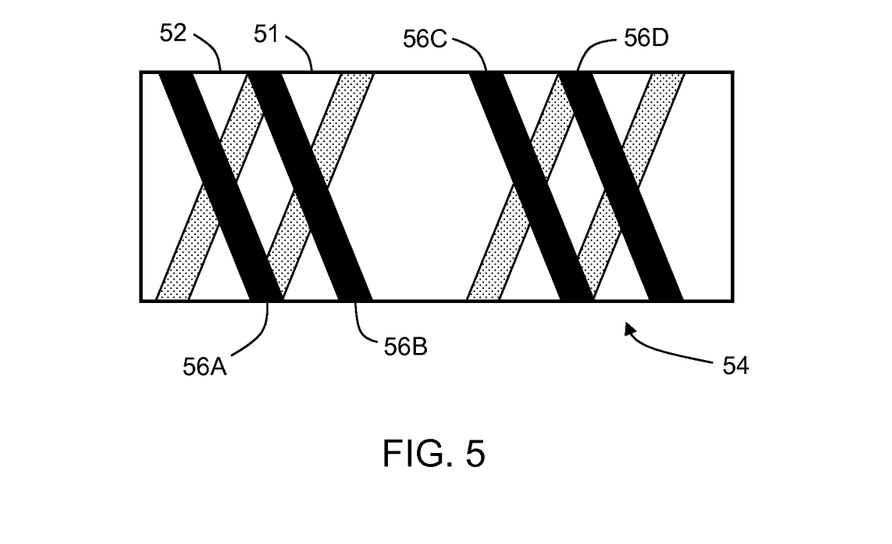
FIG. 5 is a schematic side view of an embodiment of a distal end portion of a lead.

FIG. 5 illustrates another possible arrangement of paired helical electrodes. FIG. 5 shows a distal end portion 54 of a lead, formed by a lead body 51 having a surface 52 with a plurality of electrodes 56 thereon, in this embodiment, four electrodes 56A, 56B, 56C, 56D arranged as pairs 56A, 56B and 56C, 56D. Within each pair, the electrodes are offset one half-turn or 180 degrees (i.e., electrode 56A is offset from electrode 56B, and electrode 56C is offset from electrode 56D), so that the break within each pair is 180 degrees offset. Each pair, however (i.e., electrode pair 56A, 56B and pair 56C, 56D) are situated the same. Electrodes 56A, 56B may be electrically connected to the same contact or may be separately connected to discrete contacts. Similarly, electrodes 56C, 56D may be electrically connected to the same contact or may be separately connected to discrete contacts. Similar to FIG. 3 and FIG. 4, the view in FIG. 5 is a plan side view of distal end portion 54, with stippled areas indicating portions of electrodes on the back side of the lead. Electrodes 56A, 56C wrap around body 51 one complete turn (360 degrees) from the complete front side to the complete back side, whereas electrodes 56B, 56D wrap around body 51 one complete turn (360 degrees) from the complete back side to the complete front side. In the depicted embodiment, a circumferential line anywhere between the distal most end of electrode 56A and the proximal most end of electrode 56B would intersect both electrodes 56A and 56B. Similarly, a circumferential line anywhere between the distal most end of electrode 56C and the proximal most end of electrode 56D would intersect both electrodes 56C and 56D.

Figure 6:
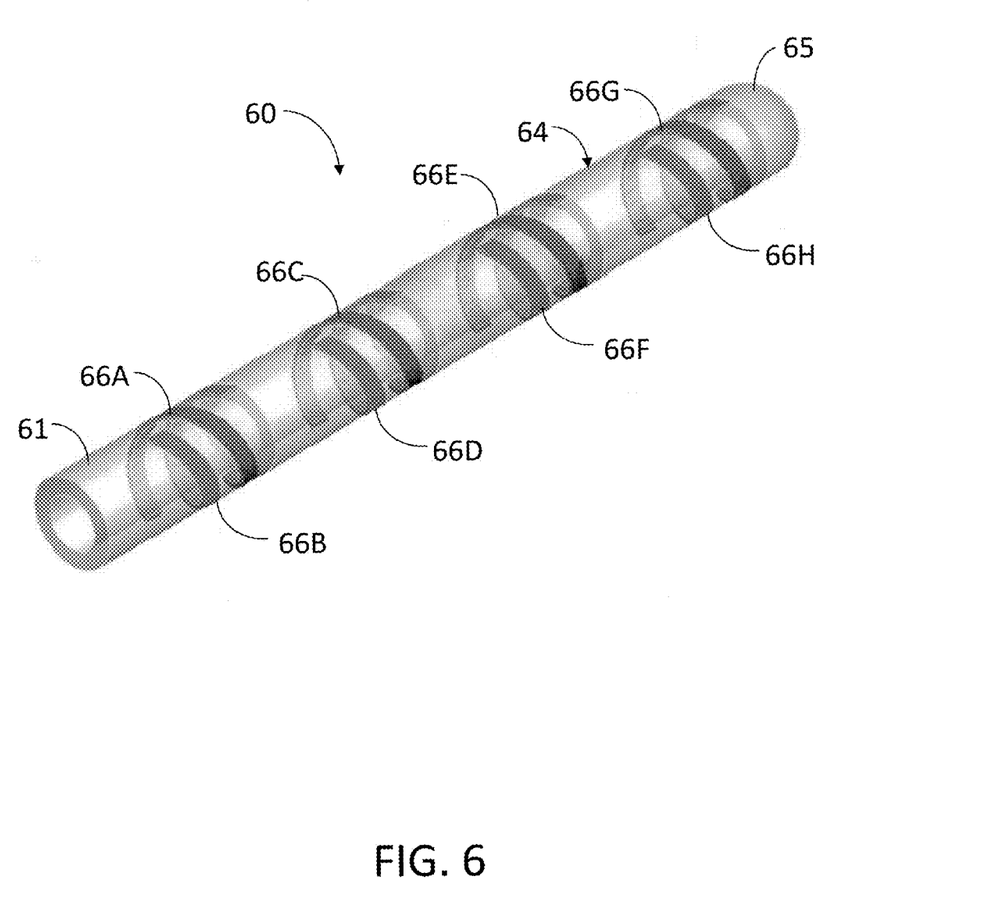
FIG. 6 is a perspective view of an embodiment of a distal end portion of a lead, showing a lead body and helical electrodes.

FIG. 6 is a perspective view of a lead 60 having a lead body 61 with a distal end portion 64 that includes a distal tip electrode 65 and a plurality of helically extending electrodes 66. Each helical electrode 66 extends one full turn or 360 degrees. In this embodiment, eight helical electrodes are provided as four pairs, specifically, electrodes 66A, 66B, 66C, 66D, 66E, 66F, 66G, 66H arranged as pairs 66A-66B, 66C-66D, 66E-66F, and 66G-66H. Within each pair, the electrodes are offset one half-turn or 180 degrees (i.e., electrode 66A is offset from electrode 66B, etc.). Each pair, however (i.e., electrode pair 66A-66B, pair 66C-66D, etc.) are situated the same. In this embodiment, electrode body 61 is about 1.5-2 mm in diameter, and adjacent electrode pairs (e.g., electrode pair 66A-66B, pair 66C-66D, etc.) have an inter-electrode pair spacing of about 3.8 mm. Each electrode (e.g., electrode

66A, 66B, etc.) is about 0.5-1 mm in width with an interelectrode spacing (e.g., spacing between electrode 66A and electrode 66B) of about 0.5-1 mm.

A helical, non-continuous electrode configuration, such as electrodes 26, 36, 46, 56, 66, provides increased surface area, improving the capability of positioning the lead against the nerve, optimizing the therapy on the nerve and minimizing energy needs (e.g., relative to a continuous helical electrode spanning the length of a distal portion of the lead). The helical arrangement of electrodes 26, 36, 46, 56, 66, enables the specific targeting of a certain fascicle or other structures or positions within the nerve. Because the arrangement of fascicle within the nerve may change along the length of the nerve, helical electrodes may be able to isolate a certain fascicle to optimize therapy.

Figure 7:
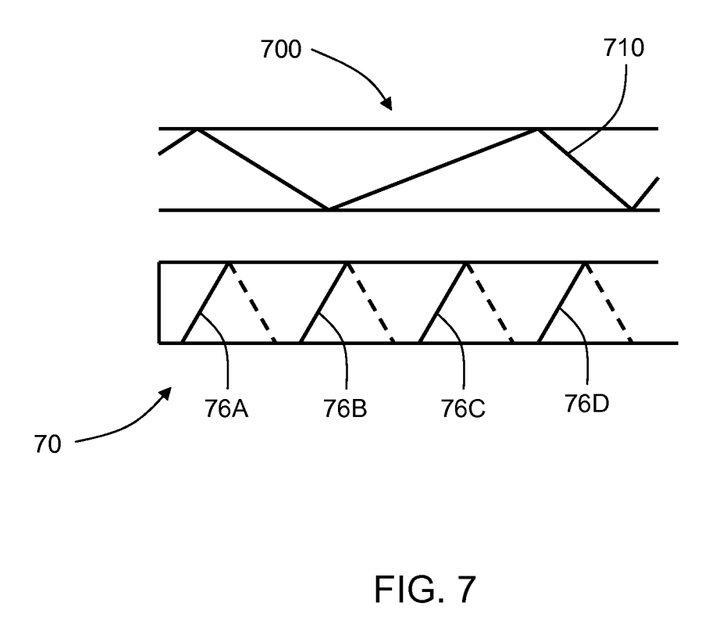
FIG. 7 is a schematic side view of an embodiment of a distal end portion of a lead implanted in proximity to a nerve.

For example, and with reference to FIG. 7, a schematic depiction of a lead 70 implanted in proximity to a nerve 700 is shown. The distal end portion of the lead 70 is implanted generally parallel to the nerve, but may be implanted in other manners relative to the nerve (e.g., transverse). The nerve 700 includes a fascicle 710 that wanders within the nerve 70 along the length of the nerve. Accordingly, while any of electrodes 76A, 76B, 76C, or 76D may be used to effectively apply an electrical signal to the nerve 700, not all of the electrodes may be used to effectively and selectively apply an electrical signal to the fascicle 710. As shown in the depicted embodiment, the portion of electrode 76B at the top of the lead 70 is closest in proximity to the fascicle 710 and may be used to selectively apply an electrical signal to the fascicle 710. Alternatively or additionally, electrodes 76A and 76B or electrodes 76A and 76C may be used in combination to selectively apply an electrical signal to the fascicle 710. If the lead migrates or rotates following implantation, a different electrode or different electrodes that selectively apply electrical signals to a desired fascicle or fascicles may readily be selected.

The helical electrode (e.g. 26, 36, 46, 56, 66, 76) configurations described herein, in most embodiments, are implanted so that the distal portion of lead having the electrodes is positioned generally parallel to the nerve to which electrical therapy will be applied. In other words, the nerve being stimulated by the lead generally extends in and along the longitudinal direction of the lead (e.g., as depicted in FIG. 7). One or more electrodes may readily be selected to selectively stimulate desired fascicles (e.g., those containing afferent fibers) of the nerve.

The leads described herein may be used for any suitable purpose, such as treatment of chronic pain associated with a peripheral nerve, such as pain associated with carpal tunnel syndrome or with hernia operations. Carpal tunnel results from the chronic entrapment of the median nerve, which is composed of many different fascicles, which typically do not remain in the same arrangement throughout the length of the nerve. Chronic pain can result if the entrapment is not relieved or if surgical intervention to relieve the entrapment causes scar tissue or mild neuropathy. Herniorrhaphy is a surgical procedure for correcting a hernia. Hernias can occur in the abdomen, groin, and at the site of a previous surgery. There are several known repairs for hernias, and chronic pain can result from all types of repair procedures. This chronic post herniorrhaphy pain can result from damage to and entrapment of nerves innervating the surgical region. The formation of neuromas, scar tissue, and misplaced mesh may also be a cause for chronic pain. The affected nerves can include the ilioinguinal, the iliohypogastric and the lateral femoral cutaneous. Leads having helical electrodes as described herein, when used as part of system 10 of FIG. 1, may be used to effectively treat chronic pain conditions. These systems are highly effective, easy to implant, safe, reliable, and easy to maintain long-term.

It will be understood that electrical signal parameters may be varied as desired for treating pain. Typically, the frequency, amplitude or pulse width of an electrical signal may be varied. An electrical signal having any suitable frequency for treating pain may be used to treat pain as described herein. For example, an electrical signal may have a frequency of about 0.5 Hz to 500 Hz (e.g., about 5 Hz to 250 Hz or about 10 Hz to 50 Hz). For example, the amplitude may be about 0.1 volts to 50 volts (e.g., about 0.5 volts to 20 volts or about 1 volt to 10 volts); for devices that the amps rather than voltage, one skilled in electronics understands the conversion from volts to amps for stimulation devices. An electrical signal may have any suitable pulse width. For example, the signal may have a pulse width of 10 microseconds to 5000 microseconds (e.g., about 100 microseconds to 1000 microseconds or about 180 microseconds to 450 microseconds). For some patients with some devices, the determination of the optimal location and parameters for stimulation occurs within days, for others, within hours or minutes.

Regardless of the use of the leads described herein, some features or aspects of some embodiments of leads having helical electrodes are provided herein. In some embodiments, the helical electrodes are configured (e.g., helix angle, electrode longitudinal width, etc.) and arranged (e.g., longitudinal inter-electrode spacing) in a manner so that any circumferential line drawn around the electrode areas of the distal end portion will intersect at least one electrode. In some embodiments, the distal end portion may include a distal-most area that is void of electrodes (as in FIG. 2) where a circumferential line drawn at the distal-most region may not hit an electrode, but otherwise, any transverse line will intersect at least one electrode. Thus, to better clarify, the electrodes are arranged in a manner so that any line drawn transverse across (including circumferentially around) distal end portion within the longitudinal area occupied by the electrodes will intersect at least one electrode. In some embodiments, at least one circumferential line drawn around the lead will intersect with two or more electrodes.

Generally, a lead as described herein will have a diameter of less than about 5 mm; e.g., between about 1-2 mm.

The helical electrodes described herein may have any suitable length, width, and exposed or active surface area. The lengths, widths and active surface areas of the electrodes of a given lead may be the same or different. In various embodiments, a helical electrode has a length of about 1 mm or greater; e.g., about 2 mm or greater. For example, the exposed length may be about 2 mm to about 20 mm (2 cm) or about 3 mm to about 10 mm (1 cm). Particular example lengths include 4 mm, 5 mm, 6, mm, 8 mm, 10 mm (1 cm), and 15 mm (1.5 cm). In some embodiments, the width of the electrodes, in the lateral direction, is about 0.1 mm to about 5 mm, in other embodiments, about 0.5 mm to about 2 mm. For some embodiments, electrode widths of about 0.25 mm (about 0.01 inch) or about 0.5 mm (about 0.02 inch) are preferred. The active surface areas of electrodes may be about 5 mm$^2$ to about 100 mm$^2$ (1 cm$^2$), about 10 mm$^2$ to about 50 mm$^2$.

The helical electrodes described herein may span any suitable longitudinal distance, and the longitudinal distances of helical electrodes in a given lead may be the same or different. By way of example, the longitudinal distance between the distal and proximal end of a helical electrode may be about 0.1 mm or greater, such as about 0.2 mm or greater. Specific examples of distance include about 0.5 mm, about 0.75 mm, about 1 mm, about 1.5 mm, and about 2 mm, although smaller and larger distances could be used.

The helical electrodes described herein may have any suitable helix angle (i.e., the angle between the helix and the axis of the lead body. For the helix angle of the electrodes may be from about 10 degrees to 80 degrees, but in most embodiments is between about 22.5 degrees and 67.5 degrees. Specific examples of suitable helix angles include 45 degrees, 60 degrees, and 75 degrees. The helix angle may be the same or different for electrodes on a lead.

Inter-electrode distances are often about 3 mm, but other inter-electrode distances may be used such as about 0.5 mm, about 1 mm, about 2 mm, about 4 mm, about 5 mm, about 6 mm, about 7 mm, about 8 mm, about 9 mm, and about 10 mm. Inter-electrode pair distances (i.e., distance between adjacent electrode pairs) are often about 3 mm, but other inter-electrode distances may be used such as about 1 mm, about 2 mm, about 4 mm, about 5 mm, about 6 mm, about 7 mm, about 8 mm, about 9 mm, about 10 mm.

Polyurethane is a preferred material for forming the lead body, although other materials such as silicone may be used. Electrical conductors extending between the proximal end and the distal end portions for supplying electrical current to the electrodes are preferably formed of coiled, braided or stranded wires comprising an electrical conductive material, e.g., MP35N or platinum-iridium alloy. The electrodes are preferably formed of platinum, although other metals and metal alloys, such as gold or stainless steel, can be used. In some embodiments, non-metallic yet electrically conductive materials may be used as the electrodes and/or electrical conductors.

One of skill in the art will understand that components described herein regarding a given embodiment or set of embodiments may readily be omitted, substituted, or added from, with, or to components of other embodiments or sets of embodiments, as appropriate or desirable.

Thus, embodiments of HELICAL ELECTRODE ARRANGEMENTS FOR MEDICAL LEADS are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical lead comprising:
a lead body having a proximal end for electrical connection to an implantable electrical signal generator and a distal end portion; and
first and second helical electrodes located at the distal end portion of the lead body, the first and second helical electrodes extending 180 degrees to 720 degrees around the lead body,
wherein the first and second helical electrodes each have a proximal end, wherein the proximal end of the first helical electrode is radially offset from the proximal end of the second helical electrode.

2. An implantable medical lead according to claim 1, comprising a plurality helical electrodes extending 180 to 270 degrees around the lead body.

3. An implantable medical lead according to claim 1, wherein each helical electrode extends 270 degrees to 540 degrees around the lead body.

4. An implantable medical lead according to claim 1, wherein each helical electrode extends 360 degrees around the lead body.

5. An implantable medical lead according to claim 1, wherein each helical electrode extends less than 360 degrees around the lead body.

6. An implantable medical lead according to claim 1, wherein each helical electrode extends more than about 360 degrees around the lead body.

7. An implantable medical lead according to claim 1, wherein when at least one circumferential line is drawn around the lead distal end portion, the circumferential line intersects with at least two helical electrodes.

8. An implantable medical lead according to claim 1, wherein the lead comprises a plurality of helical electrodes at the distal end portion of the lead body, such that when a circumferential line is drawn around the lead distal end portion anywhere between the proximal most end of the most proximal helical electrode and the distal most end of the most distal helical electrode, the circumferential line intersects with at least one of the plurality of helical electrodes.

9. An implantable medical lead according to claim 1, wherein the lead comprises a first helical electrode and a second helical electrode, each having a first end and a second end defining a break having a longitudinal distance greater than zero.

10. An implantable medical lead according to claim 9, wherein the first helical electrode is offset from the second helical electrode by about 180 degrees.

11. An implantable medical lead according to claim 9, further comprising a third helical electrode and a fourth helical electrode, each helical electrode having a first end and a second end defining a break having a longitudinal distance greater than zero.

12. An implantable medical lead according to claim 11, wherein each electrode break is offset about 90 degrees from an adjacent electrode break.

13. An implantable medical lead according to claim 11, wherein the first helical electrode and second helical electrode form a first pair and the third helical electrode and the fourth helical electrode form a second pair.

14. An implantable medical lead according to claim 13, wherein the first electrode break is offset from the second electrode break by about 180 degrees and the third electrode break is offset from the fourth electrode break by about 180 degrees.

15. An implantable medical lead according to claim 13, wherein a distance between the first pair and the second pair is about 0.5 mm to about 5 mm.

16. An implantable medical lead according to claim 15, wherein the distance between the first pair and the second pair is about 3.8 mm.

17. An implantable medical lead comprising:
a lead body having a proximal end configured to be operably connected to an implantable electrical signal generator and a distal end portion; and
a plurality of helical electrodes located at the distal end portion of the lead body, wherein each helical electrode of the plurality of helical electrodes comprises a distal end nearest the distal end portion of the lead body, and a proximal end portion nearest the proximal end of the lead body, wherein the distal end of at least one helical electrode of the plurality of helical electrodes is radially offset from the distal end of one or more of the other plurality of helical electrodes, and wherein the proximal end of at least one helical electrode of the plurality of helical electrodes is radially offset from the proximal end of one or more of the other plurality of helical electrodes, wherein each of the plurality of helical electrodes is separated from the other of the plurality of helical electrodes by a break having a longitudinal distance along the lead body that is greater than zero.

18. The implantable medical lead according to claim 17, wherein the distal ends of each of the plurality of helical electrodes are radially offset from the distal ends of at least two of the other plurality of helical electrodes or the proximal ends of each of the plurality of helical electrodes are radially offset from the proximal ends of at least two of the other plurality of helical electrodes.

19. An implantable medical lead comprising:
a lead body having a proximal end configured to be operably connected to an implantable electrical signal generator (IESG) and a distal end portion; and
first and second helical electrodes located at the distal end portion of the lead body and extending around the lead body, each helical electrode having a distal end and a proximal end, wherein the distal end of the first helical electrode is located further from the IESG than the proximal end of the first helical electrode, and the distal end of the second helical electrode is located further from the IESG than the proximal end of the second helical electrode, further wherein the distal end of the first helical electrode is located further from the IESG than the distal end of the second helical electrode along the lead body;
wherein when a circumferential line is drawn around the lead body anywhere between the distal most end of the second helical electrode and the proximal most end of the first helical electrode, the circumferential line intersects both the first and second electrodes;
third and fourth helical electrodes located at the distal end portion of the lead body and extending around the lead body each having a distal end and a proximal end, wherein the distal end of the third electrode is located further from the IESG than the proximal end of the third electrode, and the distal end of the fourth helical electrode is located further from the IESG than the proximal end of the fourth helical electrode, the third and fourth helical electrodes extending around the lead body, further wherein the distal end of the third helical electrode is located further from the IESG than the distal end of the fourth helical electrode along the lead body;
wherein when a circumferential line is drawn around the lead body anywhere between the distal most end of the fourth helical electrode and the proximal most end of the third helical electrode, the circumferential line intersects both the third and fourth electrodes; and
wherein the proximal ends of the first and second helical electrodes are radially offset from the proximal ends of the third and fourth helical electrode, and wherein each of the first, second, third and fourth electrodes extend 180 degrees to 720 degrees around the lead body.

20. An implantable medical lead comprising:
a lead body having a proximal end configured to be operably connected to an implantable electrical signal generator (IESG) and a distal end portion; and
first and second helical electrodes located at the distal end portion of the lead body and extending around the lead body, each having a distal end and a proximal end, wherein the distal end of the first electrode is located further from the IESG than the proximal end of the first electrode, and the distal end of the second helical electrode is located further from the IESG than the proximal end of the second helical electrode, further wherein the distal end of the first helical electrode is located further from the IESG than the distal end of the second helical electrode along the lead body;
wherein when a circumferential line is drawn around the lead body anywhere between the distal most end of the first helical electrode and the proximal most end of the second helical electrode, the circumferential line intersects both the first and second electrodes;
third and fourth helical electrodes located at the distal end portion of the lead body and extending around the lead body, wherein the distal end of the third electrode is located further from the IESG than the proximal end of the third electrode, and the distal end of the fourth helical electrode is located further from the IESG than the proximal end of the fourth helical electrode, wherein the distal end of the third helical electrode is located further from the IESG than the distal end of the fourth helical electrode along the lead body;
wherein when a circumferential line is drawn around the lead body anywhere between the distal most end of the third helical electrode and the proximal most end of the fourth helical electrode, the circumferential line intersects both the third and fourth electrodes; and
wherein the proximal ends of the first and second helical electrodes are radially offset from each other, and
wherein each of the first, second, third and fourth electrodes extend 180 degrees to 720 degrees around the lead body.

* * * * *

UNITED STATES PATENT AND TRADEMARK OFFICE
CERTIFICATE OF CORRECTION

PATENT NO. : 8,694,123 B2  
APPLICATION NO. : 13/376117  
DATED : April 8, 2014  
INVENTOR(S) : Carl D. Wahlstrand et al.

Page 1 of 1

It is certified that error appears in the above-identified patent and that said Letters Patent is hereby corrected as shown below:

In the Claims

Column 9, line 60: "comprising a plurality helical electrodes" should correctly read -- comprising a plurality of helical electrodes --.

Signed and Sealed this  
Twenty-first Day of April, 2015

Michelle K. Lee  
*Director of the United States Patent and Trademark Office*